United States Patent [19]
Tritsch

[11] 3,930,503
[45] Jan. 6, 1976

[54] DISPOSABLE DIAPER WITH TAB FASTENER MEANS HAVING AN INTEGRAL RELEASE SURFACE

[75] Inventor: Ludwig Tritsch, Wilmette, Ill.

[73] Assignee: Johnson & Johnson, New Brunswick, N.J.

[22] Filed: Nov. 20, 1974

[21] Appl. No.: 525,603

[52] U.S. Cl. .............................. 128/287; 128/284
[51] Int. Cl.² .............. A41B 13/02; A61F 13/16; A43C 11/00
[58] Field of Search ............... 128/284, 287, 290 R; 24/67

[56] References Cited
UNITED STATES PATENTS

| | | | |
|---|---|---|---|
| 3,642,001 | 2/1972 | Sabee | 128/287 |
| 3,810,472 | 5/1974 | Aldinger | 128/287 |
| 3,848,594 | 11/1974 | Buell | 128/284 |
| 3,875,621 | 4/1975 | Karami | 24/67 |

*Primary Examiner*—Aldrich F. Medbery

[57] ABSTRACT

A disposable diaper having a moisture-impermeable backing sheet and an absorbent pad superposed on the backing sheet is provided with tab-type fasteners which do not require a release sheet for protecting adhesive surfaces thereof. Each fastener is secured to the backing sheet and comprises a pair of terminal portions and a flexible central segment which connects the terminal portions. One of the terminal portions is attached to the backing sheet and the other, free terminal portion is releasably attached to a release surface provided on the terminal portion which is attached to the backing sheet. The flexible central segment is longer than the free terminal portion and forms a finger-receiving loop when the free terminal portion is removably attached to the release surface.

5 Claims, 4 Drawing Figures

U.S. Patent  Jan. 6, 1976  3,930,503
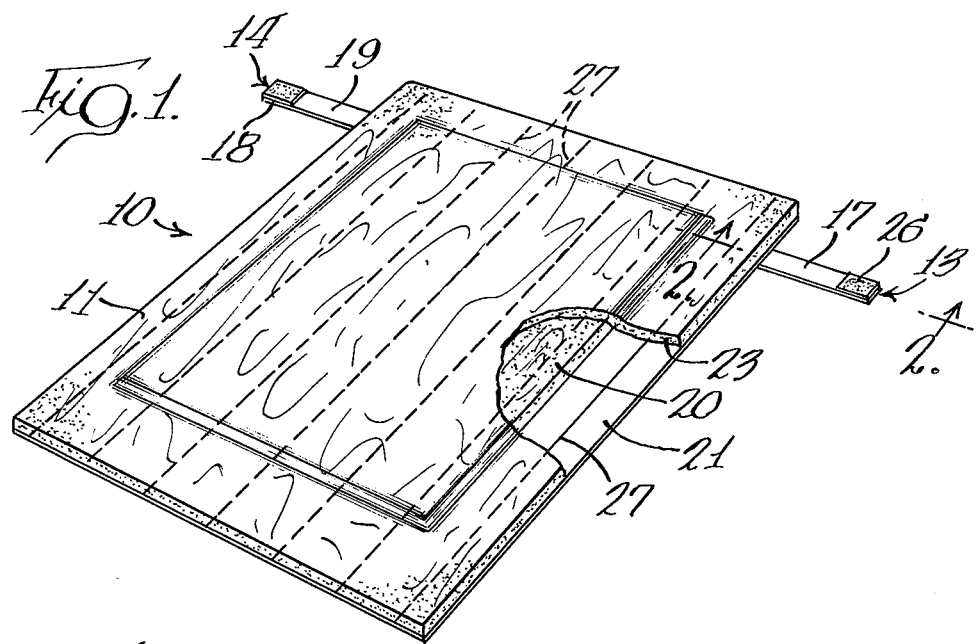
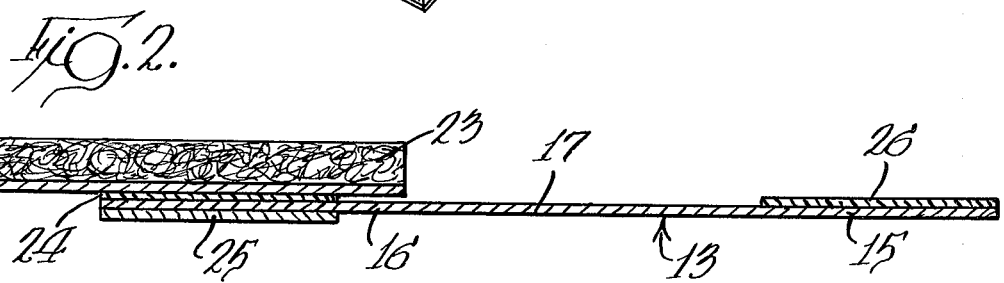
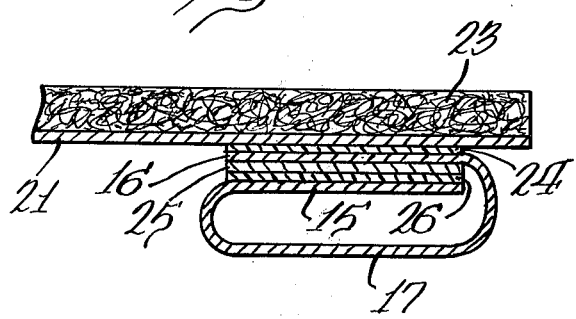
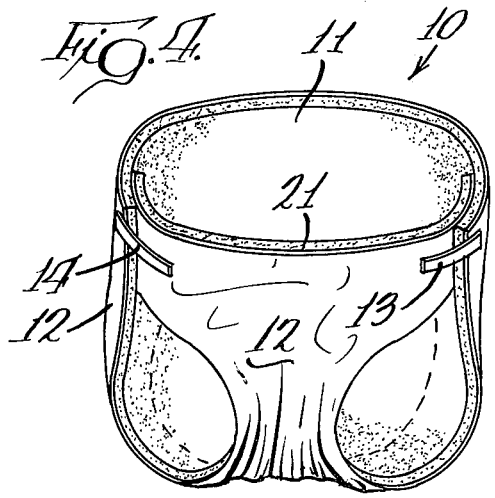

DISPOSABLE DIAPER WITH TAB FASTENER MEANS HAVING AN INTEGRAL RELEASE SURFACE

BACKGROUND OF THE INVENTION

This invention relates to disposable diapers. More particularly, this invention relates to disposable diapers adapted to be secured in place by adhesive tabs.

Disposable diapers provide substantial advantages in convenience over conventional diapers and commonly have a generally quadrilateral configuration with straight or curvilinear longitudinal edges. Disposable diapers are conveniently secured about an infant by means of adhesive tape tabs which are affixed to the diaper along a longitudinal edge thereof, thus eliminating the need for extraneous fasteners, such as pins. In order to protect the adhesive surfaces of the tape tabs, usually a release sheet is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and to adhesively attach a portion of the folded-over tab segment to the inside surface of the diaper in order to keep the tab from interfering with the manufacturing machinery and with the folding and packaging operations. This requires that the edge of the diaper backing sheet be folded over to present an attachment surface at the front or inside face of the diaper and a relatively involved tab design is necessary for this purpose. Also, undesirable tearing of the diaper facing fabric may result if such a tab is adhesively attached to the facing fabric of the diaper.

One of the most convenient adhesive systems that has been developed to date is one in which adhesive tabs are adhered to the backing sheet extending outwardly from opposite sides of the diaper at one end thereof, and in which the exposed tacky areas of the adhesive strips are provided with readily separable cover strips which protect the exposed areas until ready for use. However, disposable diapers using an adhesive closure system of this general type have the disadvantage that the consumer has to dispose of the cover strips when they are separated from the adhesive tabs. This is an inconvenience to the consumer who is placing the diaper on a baby at about the same time.

U.S. Pat. No. 3,646,937 to Gellert shows a fastening tab which is provided with a release surface which is permanently bonded to the inside surface of the diaper; however, such an arrangement is disadvantageous because the release surface may be placed in contact with the infant's skin when the diaper is used.

SUMMARY OF THE INVENTION

The present invention contemplates a diaper having an adhesive tab-type fastener which does not require a release sheet to protect the adhesive surface thereof and in which the exposed tacky surface of the fastener is removably attached to the tab itself. The disposable diaper embodying the present invention comprises a thin, flexible backing sheet of substantially moisture-impermeable material, a moisture-retaining layer including a pad of absorbent material which is superposed on the backing sheet and attached thereto, and a fastening tab means of substantially uniform width which is secured to the backing sheet and includes a pair of terminal portions and a flexible central segment which connects the terminal portions. One of the terminal portions is attached to the backing sheet and is provided with an outwardly-facing release surface, and the other, free terminal portion bears a layer of pressure-sensitive adhesive for attachment to the diaper when the diaper is applied to the infant. The free terminal portion is removably attached to the aforesaid release surface on the terminal portion which is attached to the diaper backing sheet. The central segment is longer than the free terminal portion and forms a finger-receiving loop when the free terminal portion is attached to the release surface.

BRIEF DESCRIPTION OF THE DRAWING

In the drawing,

FIG. 1 is a perspective view of a disposable diaper embodying the present invention, partially broken away to show interior construction;

FIG. 2 is a partial sectional elevation on an enlarged scale taken along plane 2—2 in FIG. 1;

FIG. 3 is a sectional elevation similar to that of FIG. 2 but showing the tab-type fastener before it is extended prior to use; and FIG. 4 is a perspective view of a disposable diaper embodying this invention in a configuration assumed by the diaper when placed about an infant.

DESCRIPTION OF THE PREFERRED EMBODIMENTS

Referring to FIGS. 1 and 4, disposable diaper 10, having a substantially quadrilateral configuration and presenting inside surface 11 for direction toward an infant and outside surface 12 for direction away from the infant is provided with adhesive tabs 13 and 14 of substantially uniform width and which can be made of polyethylene sheet, polypropylene sheet, or similar materials. As illustrated in FIG. 2 by tab 13, the fastening means comprises free terminal portion 15 and fixed terminal portion 16. These terminal portions are connected by central segment 17 which is longer than free terminal portion 15. Similarly, tab 14 is provided with a fixed terminal portion (not shown), free terminal portion 18 and central segment 19 connecting portion 18 with the corresponding terminal portion. Tabs 13 and 14 are attached to diaper 10 by securing the terminal portion, such as portion 16, to backing sheet 21 (FIG. 1) which forms outside surface 12 of the diaper. Preferably, central segment 17 is at least about 1.5 times as long as terminal portion 15.

Referring to FIG. 2, tab 13 is attached to backing sheet 21 by means of adhesive layer 24. In the case of thermoplastic tab material, attachment can also be effected by heatsealing, or similar means. The moisture-retaining layer of diaper 10, superposed on backing sheet 21, comprises absorbent pad means 20 covered by facing sheet 23. Both absorbent pad means 20 and facing sheet 23 can be secured to backing sheet 21 by means of adhesive beads 27, by heat sealing, or in any other convenient manner. Release surface 25 is provided on terminal portion 16 and faces in the same direction as the outer surface of backing sheet 21. Pressure-sensitive adhesive layer 26 is provided on free terminal portion 15 and faces in the opposite direction from release surface 25.

Before diaper 10 is prepared for use, adhesive layer 26 is protected by removable attachment to release surface 25 as shown in FIG. 3. This can be readily accomplished by simply folding central segment 17 back against diaper outside surface 11 and then folding free terminal portion 15 back against central segment 17 so that adhesive layer 26 is in juxtaposition and contacts release surface 25. Folded central segment 17 forms a finger-receiving loop, and when diaper 10 is prepared for use, terminal portion 15, bearing adhesive layer 26, is pulled free from release surface 25 of attached terminal portion 16 by inserting a finger into the formed loop and pulling toward the marginal edge of the diaper. Upon release, adhesive layer 26 faces in the same direction as diaper inside surface 11 formed by facing sheet 23 and is ready for securing the diaper in the configuration shown in FIG. 4.

In yet another embodiment of the present invention the flexible central segments such as segment 17 can be formed of an extensible elastic material, for example, rubber, a polyurethane elastomer, a butadiene-styrene block polymer elastomer, or the like. While the disposable diaper usually is relatively inelastic, the elasticity of the central segment in this particular embodiment permits the applied diaper to expand and contract about the waist of the infant, thereby accommodating the infant's movements as well as breathing action and thus contributing to comfort. The desired relative elasticity for the central segment can also be achieved by selecting an elastomeric material for the entire fastener tab means and applying relatively inelastic release and adhesive coatings on the respective terminal portions of the fastener means. The presence of such surface coatings on the terminal portions will render the terminal portions of an elastomeric material relatively less stretchable than the central segment so that the central segment will be relatively more stretchable. Also, a scrim or similar backing material can be provided for the terminal portions to render these portions less elastic than the central segment.

A suitable backing sheet for the diaper embodying the present invention can be an opaque polyethylene web about 0.001 inch thick. Another suitable sheet material for this purpose is a polyethylene terephthalate web having a thickness of about 0.0005 inch.

Several different types of facing materials may be used for diaper facing sheet 23. For example, facing sheet 23 may be made up of a mixture of fibers consisting predominantly of inexpensive short cellulosic fibers, such as wood pulp fibers or cotton linters in amounts of about 75 to about 98 percent, the balance being textile length fibers such as rayon as described in U.S. Pat. No. 3,663,348 to Liloia et al.

Facing sheet materials suitable for use in this invention have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$, is at least 0.15 lbs./in. of width in the machine direction and at least 0.1 lbs./in. of width in the cross direction. Such fabrics have unusually good elongation, loft, softness, drape characteristics in comparison to prior products incorporating any substantial amount of short fibers.

Facing sheet 23 may also be made of an apertured, nonwoven fabric which is formed, for example, in accordance with the teachings in commonly assigned U.S. Pat. Nos. 2,862,251; 3,081,514; and 3,081,515.

Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers or blends thereof. Typical facing sheets made of a polyester-type material can have a weight of ¾ oz./yd.$^2$.

Highly moisture-absorbent fibrous pad or batt 20, which is substantially rectangular in shape, but smaller than the facing and backing sheet, is centrally disposed therebetween. Pad 20 can be formed in accordance with the teachings of U.S. Pat. No. 3,612,055 to Mesek et al. Alternatively, a highly moisture-absorbent layer can be provided substantially coextensive with backing sheet 21 if desired.

Typical disposable diapers which can be fitted with a tab-type fastener described hereinabove are shown in U.S. Pat. No. 3,612,055 to Mesek et al. and in U.S. Pat. No. 3,683,916 to Mesek et al. Other suitable disposable diaper structures are shown in U.S. Pat. No. Re. 26,151 to Duncan et al.

Release properties to attached terminal portion 16 and 18 can be imparted to the outer surfaces thereof by coating these surfaces with a silicon compound, or the like, or by affixing a sheet of suitable release paper thereto.

The pressure-sensitive adhesive layers such as layer 26 and layer 28 are provided by applying a pressure-sensitive adhesive known in the art. The applied adhesive shall have good tack, good cohesive strength, good resistance to moisture and good resistance to aging. Illustrative of such adhesives are mixtures of synthetic rubber, zinc oxide, and various resins, also latices of natural or synthetic rubber, or water dispersions of acrylic tacky polymers or copolymers.

In use, a diaper equipped with the fasteners of this invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist. The removably attached terminal portions of the fastener means are then lifted from the corresponding release surfaces thereof by inserting a finger in the loops formed by the central segments of the adhesive tabs and pulling. The tabs are adhesively fixed in a desired position on the backing sheet of the abdomen-covering end by simply continuing the finger motion so as to urge the pressure-sensitive adhesive surfaces in contact with an underlying backing sheet region.

The foregoing description and the drawing are illustrative but are not to be taken as limiting. Still other variations and modifications are possible without departing from the spirit and scope of the present invention.

I claim:

1. In combination with a disposable diaper of substantially quadrilateral configuration, having an inside surface for direction toward an infant when the diaper is worn by that infant and an outside surface for direction away from said infant and including a thin, flexible backing sheet of substantially moisture-impermeable material and a moisture retaining layer having a pad of absorbent material superposed on said backing sheet and attached thereto, a fastening tab means of substantially uniform width and comprising a pair of terminal portions and a flexible central segment connecting the terminal portions; one of said terminal portions being attached to said backing sheet and having an outwardly-facing release surface, the other free terminal portion bearing a layer of pressure-sensitive adhesive for attachment to the outside surface of the diaper when the diaper is applied to the infant and being adapted for removable attachment to said release surface by means of the adhesive layer thereon, and said central segment being longer than said free terminal portion and forming a finger-receiving loop when said free terminal portion is removably attached to said release surface; said release surface on the attached terminal portion and said adhesive layer on the free terminal portion being situated on opposite sides of said fastening tab means.

2. The combination in accordance with claim 1 wherein said central segment is at least about 1.5 times as long as said free terminal portion.

3. The combination in accordance with claim 1 wherein said terminal portion is adhesively attached to said backing sheet.

4. The combination in accordance with claim 1 wherein said central segment is folded back against the diaper outside surface and wherein said free terminal portion is folded back against the central segment so that the adhesive layer on said free terminal portion is in juxtaposition with and releasably attached to said release surface.

5. The combination in accordance with claim 1 wherein said central segment is an extensible elastic material which is more stretchable than said terminal portions.

* * * * *